(12) United States Patent
Holzner et al.

(10) Patent No.: US 8,408,902 B2
(45) Date of Patent: Apr. 2, 2013

(54) MATERIAL AND BLANK FOR DENTURES

(75) Inventors: Stephan Holzner, Hohenschäftlarn (DE); Gerhard Weber, Pürgen (DE)

(73) Assignee: Institut Straumann AG, Basel (CH)

( * ) Notice: Subject to any disclaimer, the term of this patent is extended or adjusted under 35 U.S.C. 154(b) by 844 days.

(21) Appl. No.: 12/306,045

(22) PCT Filed: Jun. 18, 2007

(86) PCT No.: PCT/EP2007/005360
§ 371 (c)(1),
(2), (4) Date: Aug. 31, 2009

(87) PCT Pub. No.: WO2007/147549
PCT Pub. Date: Dec. 27, 2007

(65) Prior Publication Data
US 2010/0015573 A1      Jan. 21, 2010

(30) Foreign Application Priority Data

Jun. 23, 2006    (EP) .................................. 06012980

(51) Int. Cl.
| A61C 13/00 | (2006.01) |
| A61C 13/06 | (2006.01) |
| A61C 8/00 | (2006.01) |
| C04B 35/48 | (2006.01) |
| C04B 35/49 | (2006.01) |
| C09K 3/00 | (2006.01) |

(52) U.S. Cl. .................. 433/171; 433/201.1; 433/202.1; 501/103; 106/36

(58) Field of Classification Search .......... 501/102–105; 105/35; 433/171, 201.1, 202.1, 218, 219
See application file for complete search history.

(56) References Cited

U.S. PATENT DOCUMENTS

| 5,125,970 A * | 6/1992 | Klepacki ......................... 106/35 |
| 5,125,971 A * | 6/1992 | Nonami et al. .................. 106/35 |
| 5,776,382 A * | 7/1998 | Kim et al. ....................... 264/16 |
| 5,968,856 A * | 10/1999 | Schweiger et al. ............... 501/7 |
| 6,354,836 B1 | 3/2002 | Panzera et al. |
| 6,409,852 B1 | 6/2002 | Lin et al. |
| 6,713,421 B1 | 3/2004 | Hauptmann et al. |

(Continued)

FOREIGN PATENT DOCUMENTS

| CA | 2322761 | 10/2007 |
| CN | 1489988 A | 4/2004 |

(Continued)

OTHER PUBLICATIONS

European Communication in corresponding EP 07 726065.1 mailed Apr. 23, 2009, and English translation thereof.

(Continued)

*Primary Examiner* — Kaj K Olsen
*Assistant Examiner* — Noah Wiese
(74) *Attorney, Agent, or Firm* — Rissman Hendricks & Oliverio LLP

(57) ABSTRACT

A material for dentures having a 3-point bending strength of at least 1300 MPa, dentures produced from said type of material, corresponding blank materials, a method for producing blanks, and a method for producing a denture part made from said material or a blank.

5 Claims, 3 Drawing Sheets

U.S. PATENT DOCUMENTS

| | | | |
|---|---|---|---|
| 7,604,759 B2 | 10/2009 | Brodbeck et al. | |
| 2002/0006532 A1* | 1/2002 | Robin | 428/697 |
| 2004/0119180 A1* | 6/2004 | Frank et al. | 264/16 |
| 2004/0197738 A1* | 10/2004 | Ban et al. | 433/202.1 |

FOREIGN PATENT DOCUMENTS

| | | |
|---|---|---|
| EP | 0140638 A1 | 5/1985 |
| EP | 0218853 A1 | 4/1987 |
| EP | 0624360 A1 | 11/1994 |
| EP | 0630622 A2 | 12/1994 |
| EP | 140 638 A1 | 5/1995 |
| WO | WO 97/30654 A1 | 8/1997 |
| WO | WO 9947065 A1 | 9/1999 |
| WO | WO 01/12132 A1 | 2/2001 |
| WO | WO 02/064099 | 8/2002 |
| WO | WO 02064099 A1 | 8/2002 |
| WO | WO 02/074714 A1 | 9/2002 |
| WO | WO 02/085242 A1 | 10/2002 |
| WO | WO 2004086999 A1 | 10/2004 |

OTHER PUBLICATIONS

International Search Report in corresponding PCT/EP2007/005360 mailed Aug. 2, 2007.

Kosmac T. et al., "Strength and Reliability of Surface Treated Y-TZP Dental Ceramics", Journal of Biomedical Materials Research, Wiley, New York, NY, pp. 304-313 (2000).

Sep. 12, 2012 EPO Communication regarding filing of two oppositions by Degudent GMBH and Ivoclar Vivadent AG on Sep. 7, 2012 against EP Patent 2034947 (EP Application 07726065.1).

Filser, F. et al. "All Ceramics Dental Bridges by Direct Ceramic Machining (DCM)", Materials in Medicine, 1998, pp. 165-189.

* cited by examiner

MATERIAL AND BLANK FOR DENTURES

The present invention relates to starting materials and blanks for producing denture parts.

Denture parts can be produced by means of automated manufacturing methods from raw materials, such as ceramics or metals. The denture parts are here e.g. milled from solid materials. In the case of ceramic materials the milled denture parts are normally subjected to dense sintering so as to obtain denture parts of a high breaking strength.

It is the object of the present invention to improve the starting materials of denture parts, blanks and associated methods and thus also the denture parts.

Preferred embodiments are disclosed in the dependent claims.

It has been found out in elaborate studies that it is possible to provide a material for a denture that has a 3-point bending strength of at least 1300 MPa. The material is preferably a ceramic material such as zirconium oxide or comprises zirconium oxide. Instead of zirconium oxide, the term zirconium dioxide is often used for the same material.

All information given on a 3-point bending strength in this document refers to the 3-point bending strength defined in the ISO 6872 standard.

Furthermore, a material is of advantage that has a 3-point bending strength of at least 1400, 1500, 1600, 1700, 1800, 1900 or 2000 MPa. The higher the 3-point bending strength, the greater is the loadability of denture parts that were made from such material, so that denture parts become feasible with thinner wall thicknesses or denture parts withstanding greater loads.

Furthermore, it is of advantage when the material shows density variations of less than 10%, 5% or 2%. Such density variations lead to an inhomogeneous pressure resistance so that it may happen that the material only exhibits a low density and thus a low breaking resistance in a disadvantageous way exactly at a highly loaded place of the denture part.

Furthermore, the material can contain a high content of zirconium oxide and at least a certain content of yttrium oxide. Furthermore, hafnium oxide may be added and/or a metal oxide or metal salt.

The material can e.g. have a zirconium oxide content of more than 90%, 92%, 94%, 96% or 97%, but not more than 92%, 94%, 96%, 98% or 99%. Hafnium oxide may not be present at all or it may be present with at least 0.5%, 1%, 1.5%, 2%, 2.5%, 3% and/or with not more than 0.5%, 1%, 1.5%, 2%, 2.5%, 3%, 3.5%, 4%. Yttrium oxide is present at an amount of more than 1.5%, 2%, 2.5%, 3%, 3.5%, 4%, 4.5%, 5% and/or at an amount of not more than 2%, 2.5%, 3%, 3.5%, 4%, 4.5%, 5%, 5.5%, 6%.

Furthermore, one or more of the oxides of aluminum, gallium, germanium, indium, tin, lead, lanthanides, metals, iron and/or one or a plurality of metal salts may be present at an amount of at least 0.01%, 0.02%, 0.05%, 0.1%, 0.2%, 0.3%, 0.4%, 0.5% and/or at an amount of not more than 0.1%, 0.2%, 0.3%, 0.4%, 0.5%, 0.6%, 0.7%, 0.75%.

The percentage values indicated in this document for the chemical composition refer to weight percent.

The last-mentioned oxides or salts have been distributed as homogeneously as possible in the manufacture of the material, resulting in crystal nuclei and thus crystallite sizes that are as homogeneous as possible. Furthermore, the orientations of the crystallization axes can thereby be influenced, namely such that they are distributed as uniformly as possible in all spatial directions, so that dense sintering, by which the denture part will then be produced, results in a contraction of the material in all spatial directions of the same magnitude.

Dense sintering is e.g. carried out at temperatures between 1200° C. and 1600° C., e.g. at about 1400° C. for a period of time of 10 to 16 hours. Dense sintering is preferred at 1400° C. for 14 hours. Furthermore, dense sintering is preferably carried out at ambient pressure because this is feasible with relatively simple furnaces. However, an increased pressure may also prevail during sintering (up to 200 bar). This means that e.g. the maximum pressing pressure is applied at room temperature or at a temperature of less than 50° C., 100° C., or 200° C. Moreover, the whole pressing operation can be carried out at room temperature or at a temperature of less than 50° C., 100° C. or 200° C.

The denture part consists of one of the materials listed above or further below.

The invention further relates to a material for a blank for producing dentures. The material is changed by dense sintering into a material for dentures and in the way as described above and further below. This blank material has a bending strength of at least 20 MPa and not more than 180 MPa, and all intermediate values or intermediate intervals are feasible. The lower the 3-point bending strength, the easier becomes the machining of the material, for instance, by way of milling and without any great wear of the milling tool. The higher the bending strength, the greater the loads the material can withstand during milling, thereby permitting a faster milling operation. Within the said interval a good compromise is found between the different requirements.

The chemical composition of this blank material corresponds to the composition of the material for dentures because the chemical composition does not change during dense sintering.

A blank for producing dentures preferably comprises a material as indicated above for a blank for producing dentures.

Furthermore, a blank for producing dentures is characterized in that the material or the blank was pressed at a pressing pressure of at least 1500 bar isostatically or uniaxially or biaxially or triaxially.

It exhibits a density of 3.10-3.30 g/cm$^3$, preferably 3.15-3.25 g/cm$^3$.

It has been found that due to the pressing operation at a very high pressing pressure the blank material shows a very great 3-point bending strength after dense sintering. Although the density after dense sintering is virtually independent of the pressing pressure for the blank, this surprisingly leads to an improvement of the 3-point bending strength due to a high pressing pressure. The temperature is room temperature or less than 50° C., 100° C. or 200° C. during the whole pressing operation or at maximum pressure, respectively.

The thickness [sic] of the dense sintered material is preferably 6.00-6.10 g/cm$^3$ or 6.05-6.07 g/cm$^3$.

It has particularly been found that with a large blank body, from which several blanks can be made, the 3-point bending strength is very reliably achieved for all blanks of the blank body. The variation of the 3-point bending strength within a blank body produced in this way is relatively small.

The pressing pressure can also be higher than 1500 bar, i.e. up to 3000 bar or 4000 bar. The material for producing the blank can be pressed at ambient temperature or also at an elevated temperature, e.g. 50° C., 100° C. or 200° C.

The blank is preferably shaped in the form of a plate, and a circular, square, rectangular or polygonal plate shape has here turned out to be of advantage to further processing for obtaining denture parts from the blank.

On the plate side, a marking may be provided by way of a groove or a colored or otherwise designed marking with which the orientation of the blank can be clearly defined.

Furthermore, it is advantageous when the plate side is without steps as this will yield a simple geometric shape of the blank. When denture parts are produced, the denture parts must be shaped out of the blank on an enlarged scale as the material will contract in the subsequent dense-sintering operation. The magnification factor corresponds here to the third root of the quotient of the target density and the pre-sintering density. Since the plate side is without any steps, the volume of the plate can be determined as exactly and easily as possible by measuring the size of the blank, so that the pre-sintering density can also be determined as exactly and easily as possible.

As has already been mentioned above, the manufacture of a blank for producing dentures by pressing at a high pressing pressure yields a highly homogeneous blank material. That is why a set of blanks, particularly blanks of one and the same blank body, will be shown hereinafter, wherein the blanks may have a 3-point bending strength of at least 1300 MPa to 2000 MPa by way of dense sintering.

Furthermore, a set of blanks of one and the same blank body is characterized in that the blank body was pressed at a pressing pressure of at least 1500 bar isostatically, uniaxially, biaxially or triaxially.

Moreover, the invention relates to a method for producing blank bodies or blanks for producing dentures. In the method a powder is pressed at an isostatic or uniaxial, biaxial or triaxial pressing pressure of at least 1500 bar into a blank body. The pressure may here be 4100 bar or assume an intermediate value between 1500 bar and 4100 bar or may be present in all intermediate intervals between 1500 bar and 4100 bar.

Such a blank body or blank produced in this way may show a 3-point bending strength in the range of between 20 MPa and 180 MPa or all intermediate values or of possible intermediate intervals between said values. The blank material is thereby machinable. The dense sintering of this material will yield a 3-point bending strength of at least 1300 MPa to 2000 MPa.

In the method the powder is for instance filled into a rubber-elastic body for pressing purposes. The filling operation is preferably carried out in a cleanroom, so that undesired impurities of the powder are kept as small as possible.

The powder may be an oxide with a metal salt being possibly admixed, as has been stated further above.

The pressing operation is preferably carried out in a hydrostatic press with which an isostatic pressing of the powder is made possible. Such a pressed powder yields a blank with a very homogeneous density of a good material contraction during dense sintering in such a way that the contraction in the different spatial directions is the same. The pressing operation yields a blank body which as a rule does not show an entirely uniform shape. To be more specific, an isostatic pressing operation will yield a blank body with a corrugated surface. It is therefore advantageous to turn or face such a blank body after pressing. The turning operation yields a circular cylindrical shape. During the facing operation surfaces of the blank body are treated such that they are subsequently even or planar. This leads, for instance, to blank bodies with a square or rectangular cross-section when the different planes that have been formed are perpendicular to each other, or to another polygonal cross-section.

In the method the blank body is preferably divided into a plurality of blanks. This is preferably carried out by way of a separating operation along planes that are preferably in parallel with each other and approximately perpendicular to a longitudinal axis of the blank body; with the method, however, it is also possible to produce blanks immediately and not at first blank bodies that are then separated. Moreover, it is possible to produce a plurality of blank bodies in a single pressing operation separately, each in a separate rubber-elastic body.

Furthermore, such a method is of advantage wherein the blank body is provided along a longitudinal axis of said blank body with a marking. The marking may be a groove or a colored or otherwise designed line. Also bar codes, or the like, can here be applied to the blank body.

The present invention also relates to a method for producing a denture part using one of the described blanks or a blank produced according to the described methods. The machining operation is preferably milling.

In any one of the above methods or blanks or materials, ambient temperature or a temperature of less than 50° C., 100° C. or 200° C. may prevail during the whole pressing operation or at the maximum pressure.

Ambient pressure preferably prevails during the whole sintering operation or at the maximum temperature. However, an overpressure of not more than 1, 2, 5, 10, 20, 50 or 200 bar may also prevail.

During sintering the object to be sintered, e.g. a material, a blank or a denture part, is preferably not packed. Rather, it may be present in bulk form in a furnace. To be more specific, a liquid-tight package is not provided.

Advantageous embodiments of the invention shall now be explained with reference to the figures, of which:

FIG. 1 shows a hydrostatic press 1 into which a rubber-elastic body 5 is inserted, which in turn is filled with a powder, such as zirconium oxide powder, and additives.

Figure 1:
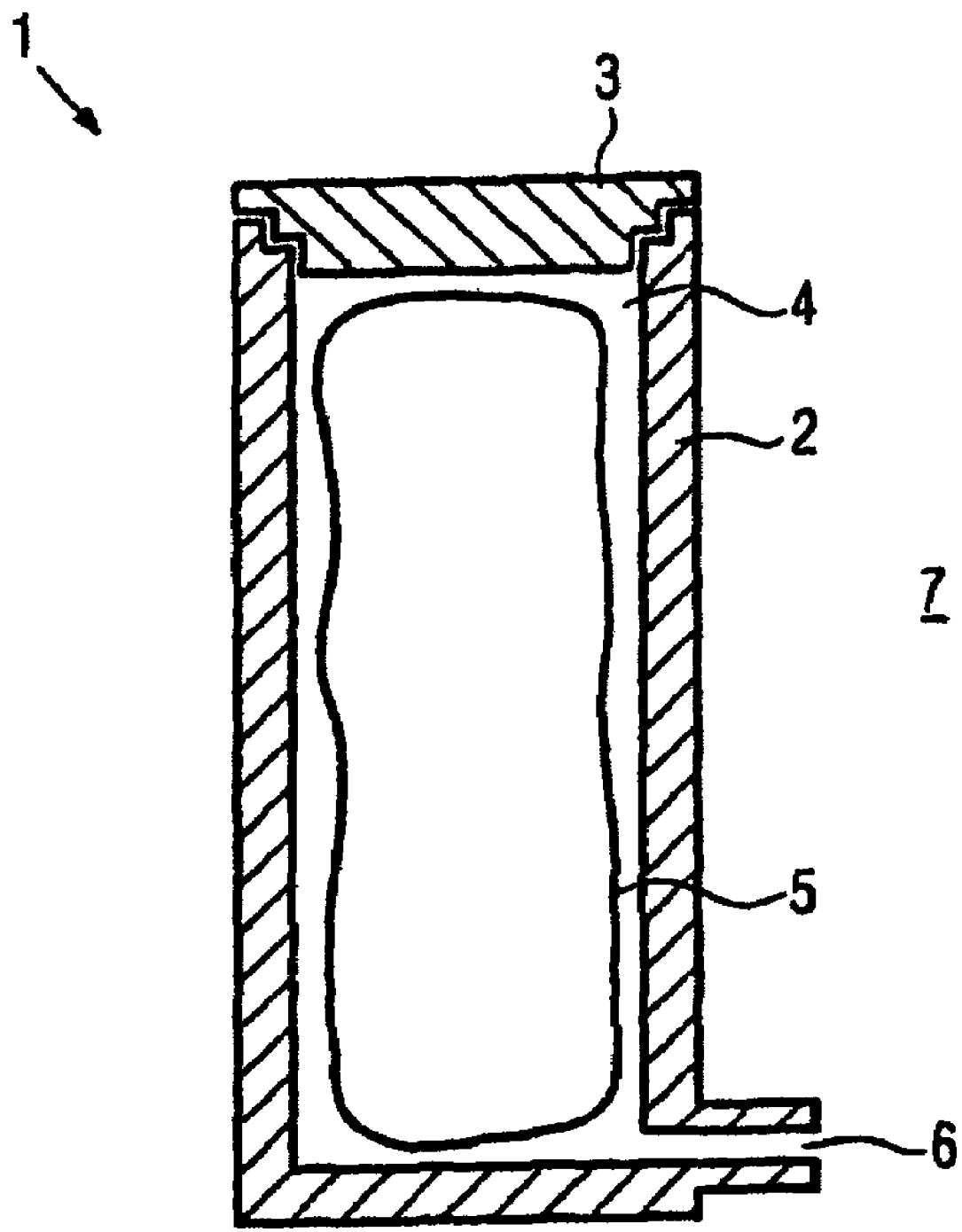
FIG. 1 is a schematic sectional view of an isostatic press.

The rubber-elastic body 5 is positioned in an interior 4 created by a container 2 and a lid 3. Hydrostatic pressure can be exerted through a feed line 6 on the rubber-elastic body 5 and thus on the powder located in the rubber-elastic body 5.

The rubber-elastic body 5 was filled with powder in a cleanroom 7 and closed.

Figure 2:
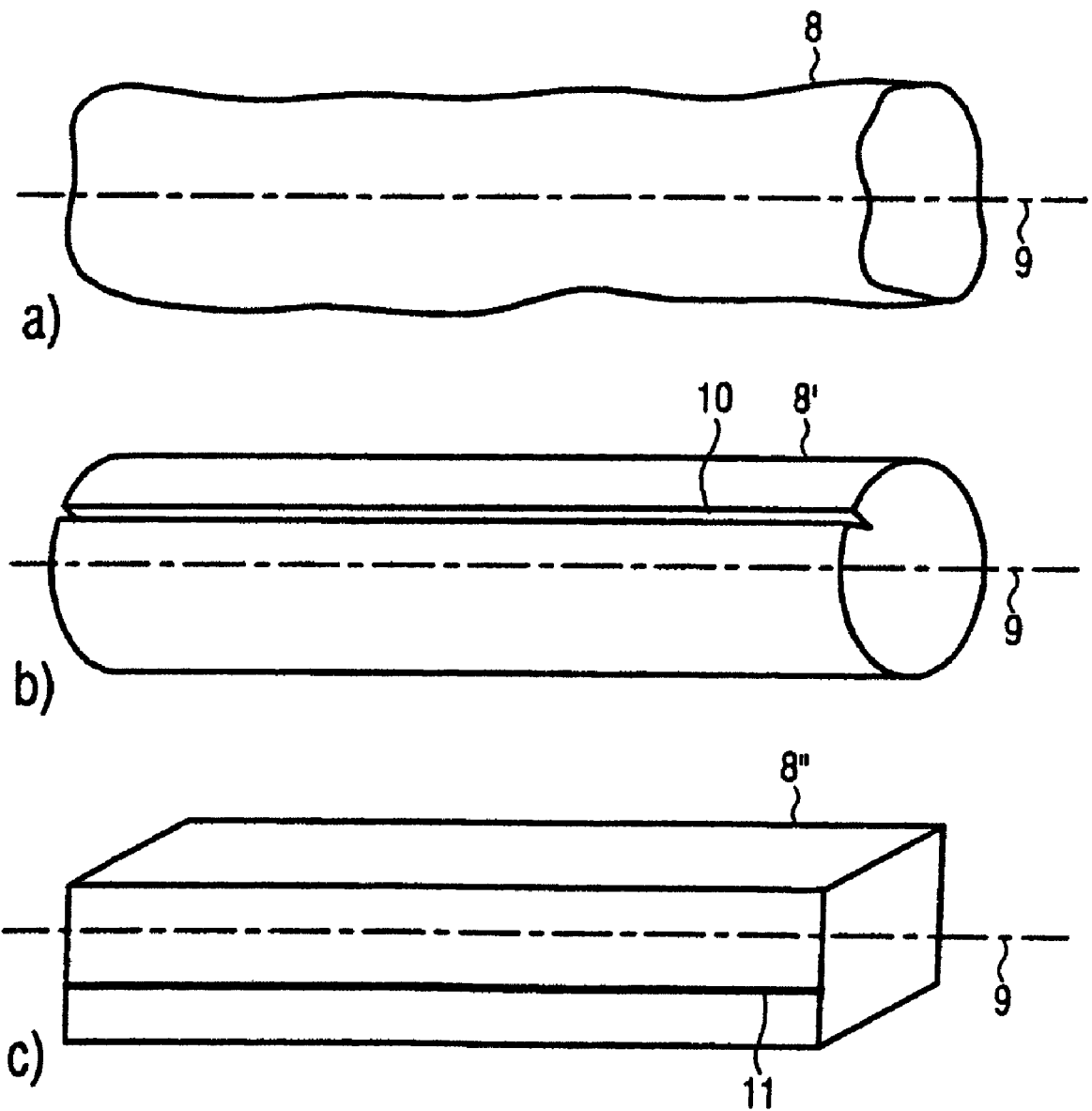
FIG. 2 shows three-dimensional schematic views of blank bodies.

A blank body obtained with the hydrostatic press of FIG. 1 is schematically shown in FIG. 2a. The blank body 8 has a longitudinal axis 9 and also a slightly irregularly corrugated surface. The blank 8 can be reworked into a rotation-symmetrical blank body 8' (see FIG. 2b) by turning the same. A groove 10 with which blanks are assigned or recognized in their position after division of the blank body 8' may also be provided in this blank body 8'. To this end a groove with an asymmetric cross-section or a plurality of asymmetrically grooves is/are of particular advantage.

The hydrostatic press is working at ambient temperature. Elevated temperatures of up to 50° C., 100° C. or 200° C. are however also possible.

FIG. 2c shows a preferred embodiment of such a blank body 8", which was faced for obtaining a square or rectangular cross-section. The blank body is provided with a groove or marking 11 that is preferably arranged such that it is not positioned on a symmetry plane or axis of the blank body 2a, so that the position of the blank obtained from said blank body 8" can be recognized in a definite way. An asymmetrically arranged groove and/or a plurality of asymmetrically arranged grooves are here also of advantage.

Figure 3:
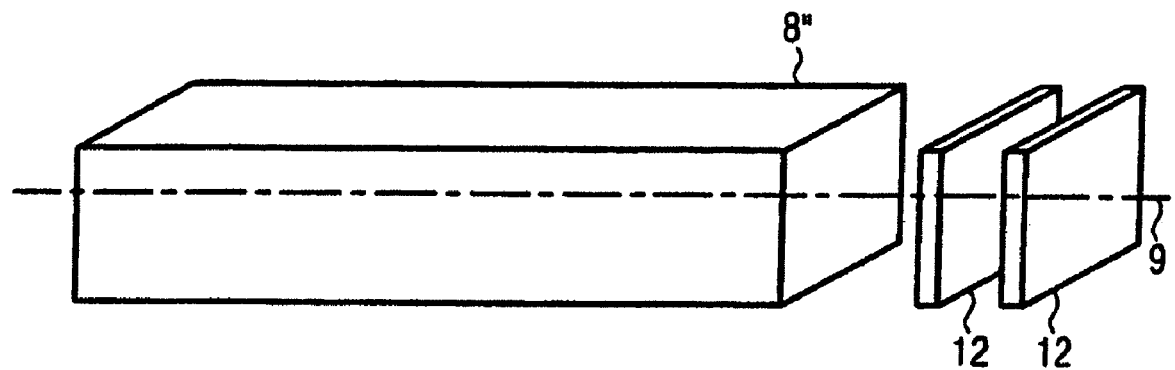
FIG. 3 is a three-dimensional schematic view of a blank body and blanks obtained therefrom.

FIG. 3 shows by way of example how the blank 8" is divided into individual blanks 12 by separation along planes in a direction perpendicular to the axis 9.

Instead of first obtaining blank bodies 8 that are then divided, it is also possible to press blanks immediately. The separation into blanks can then be omitted. As a rule, the surfaces of blanks obtained by pressing will also be slightly irregular so that here a facing operation is recommended for these surfaces in order to obtain blanks having simple geometric shapes.

Figure 4:
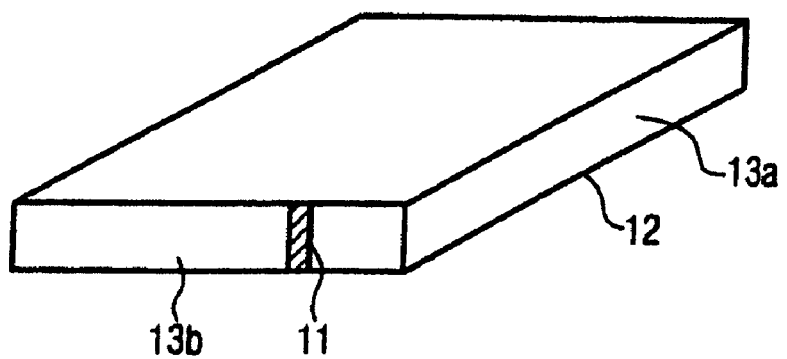
FIG. 4 is a three-dimensional schematic view of a blank.

FIG. 4 schematically shows a blank 12. Said blank has the shape of a plate with plate sides 13*a* and 13*b*.

The sides 13*a* and 13*b* are stepless, i.e. in the direction from the upper to the lower side the side is without steps. In a direction perpendicular thereto, steps may be provided e.g. by way of a groove.

On the side 13*b* a marking can be seen that corresponds to the marking 11 of FIG. 2*c*. Since this marking is not centrally provided on the side 13*b* (this would however also be possible), the position of blank 12 can clearly be made out by finding the marking 11. For instance, when the blank is rotated by 180°, namely about an axis located in the plane of the plate and passing through the area 13*b*, the marking 11 is positioned further to the left instead of, as shown in FIG. 4, further to the right when seen from the center. Furthermore, the marking 11 marks one of the four plate sides, so that the position of the blank 12 can clearly be determined with the marking 11.

Such a blank, as shown in FIG. 4, has a 3-point bending strength between 20 MPa and 180 MPa. After the dense sintering of such a blank or a denture part obtained from said blank, for instance by milling, one obtains a material exhibiting a 3-point bending strength of at least 1300 MPa.

Here values of up to more than 1500 or even more than 1600 and 1700, 1800 or even more than 1900 MPa are possible.

These values are also achievable when the dense sintering operation is carried out at ambient pressure. A slightly increased pressure of up to 1, 2, 5, 10, 20, 50, 100 or 200 bar is however also possible.

The invention claimed is:

1. Method for producing a denture part or denture parts, comprising the steps of:
   a) producing blanks or blank bodies by pressing of a powdery ceramic material with an isostatic or uniaxial, biaxial or triaxial pressing pressure of at least 1500 bar and not more than 4100 bar into a blank or a blank body, wherein at the maximum pressing pressure or throughout the pressing operation room temperature or a temperature of less than 200° C. is applied, such that the blank or the blank body has a 3-point bending strength between 20 MPa and 180 MPa after the pressing, and wherein the blank body is divided into a plurality of blanks; or
   providing a blank, whereby the blank is obtained by pressing of a powdery ceramic material with an isostatic or uniaxial, biaxial or triaxial pressing pressure of at least 1500 bar and not more than 4100 bar into a blank or a blank body, wherein at maximum pressing pressure or throughout the pressing operation room temperature or a temperature of less than 200° C. is applied, such that the blank has a 3-point bending strength between 20 MPa and 180 MPa after the pressing: or
   providing a set of blanks obtained from one and the same blank body, wherein the blank body is obtained by pressing of a powdery ceramic material with an isostatic or uniaxial, biaxial or triaxial pressing pressure of at least 1500 bar and not more than 4100 bar, wherein at the maximum pressing pressure or throughout the pressing operation room temperature or a temperature of less than 200° C. is applied, such that the blank body has a 3-point bending strength between 20 MPa and 180 MPa after the pressing;
   b) machining the blank or the blanks of the set of blanks to form a denture part or a plurality of denture parts;
   dense sintering the denture part or the plurality of dentures parts after step b) at a temperature between 1200° C. and 1700° C. for a period of 10 hours to 16 hours, wherein after the dense sintering the ceramic material has a 3-point bending strength of at least 1300 MPa up to 2000 MPa.

2. The method according to claim 1, wherein the whole dense-sintering operation or the application of the maximum pressure is carried out at ambient pressure or at an overpressure of less than 1, 5, 10, 20, 50, 100 or 200 bar.

3. The method of claim 1, wherein the blank body is divided into the plurality of blanks by separation along a plane.

4. The method of claim 3, wherein the plane is approximately perpendicular to a longitudinal axis of the blank body.

5. The method of claim 1, wherein the machining is performed by milling.

\* \* \* \* \*